US012558131B2

(12) United States Patent
Soo

(10) Patent No.: US 12,558,131 B2
(45) Date of Patent: Feb. 24, 2026

(54) INTRAARTICULAR SPACER FOR STABILIZING AN ILIUM AND A SACRUM

(71) Applicant: Cheng-Lun Soo, Oklahoma City, OK (US)

(72) Inventor: Cheng-Lun Soo, Oklahoma City, OK (US)

( * ) Notice: Subject to any disclaimer, the term of this patent is extended or adjusted under 35 U.S.C. 154(b) by 42 days.

(21) Appl. No.: 18/486,592

(22) Filed: Oct. 13, 2023

(65) Prior Publication Data

US 2025/0120752 A1     Apr. 17, 2025

(51) Int. Cl.
*A61B 17/70*       (2006.01)
*A61F 2/30*        (2006.01)

(52) U.S. Cl.
CPC ...... *A61B 17/7055* (2013.01); *A61F 2/30988* (2013.01); *A61F 2002/30995* (2013.01)

(58) Field of Classification Search
CPC .................. A61B 17/7055; A61F 2002/30995
See application file for complete search history.

(56) References Cited

U.S. PATENT DOCUMENTS

| | | | |
|---|---|---|---|
| 8,292,955 B2 * | 10/2012 | Robinson .............. | A61F 2/4606 623/14.12 |
| 8,764,829 B2 * | 7/2014 | Marvel ................. | A61F 2/4618 623/14.12 |
| 8,858,597 B2 * | 10/2014 | Blain ........................ | A61F 2/46 606/247 |
| 8,945,224 B2 * | 2/2015 | Trieu ................. | A61B 17/7055 623/17.12 |
| 2011/0098816 A1 * | 4/2011 | Jacob ................. | A61B 17/7055 623/17.11 |

* cited by examiner

*Primary Examiner* — Christian A Sevilla
(74) *Attorney, Agent, or Firm* — Edward L. White, PC

(57) ABSTRACT

A method and intraarticular spacer for stabilizing an ilium and a sacrum at a sacroiliac joint, the intraarticular spacer includes a body defining an exterior surface that includes at least one anchor adapted to engage the sacrum and the ilium, a proximal end smaller than a distal end, at least one aperture, and an exterior channel. The distal end includes a driver engagement. The anchor may include a thread on the exterior surface arranged longitudinally about a central axis of the body. The intraarticular spacer may include more than one prong adapted to engage the sacrum and ilium, a stabilizing material, and a central bore extending longitudinally about a central axis of the body, the central bore defining an interior surface and including an interior thread coupled to the interior surface.

21 Claims, 9 Drawing Sheets

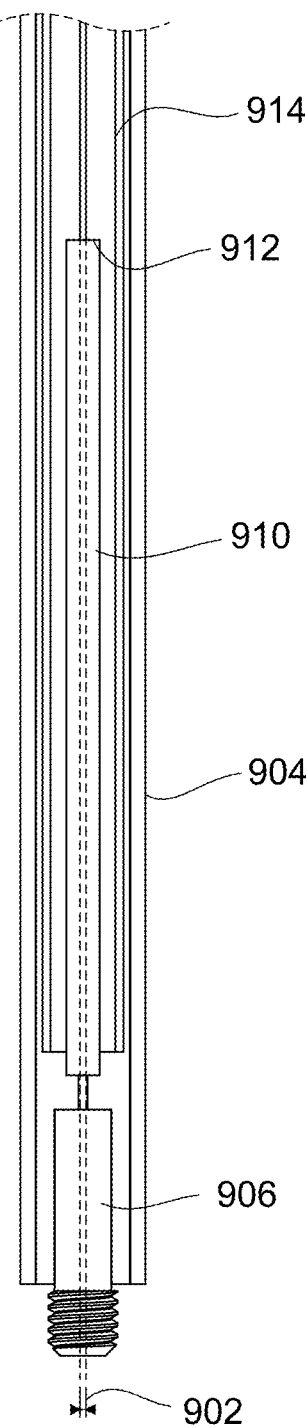
914
912
910
904
906
902
(NEW)
FIG. 9

INTRAARTICULAR SPACER FOR STABILIZING AN ILIUM AND A SACRUM

CROSS-REFERENCE TO RELATED APPLICATIONS

None.

BACKGROUND

This section is intended to introduce the reader to various aspects of art that may be related to various aspects of the presently described embodiments. This discussion is believed to be helpful in providing the reader with background information to facilitate a better understanding of the various aspects of the present embodiments. Accordingly, it should be understood these statements are to be read in this light and not as admissions of prior art.

This invention generally relates to medical devices and medical methods to repair musculoskeletal structures. Particularly, the present invention relates to musculoskeletal surgical methods and surgical implants for treatment and repair of the sacroiliac joint. Such surgery may include implants such as intraarticular spacers or plate/rod and screw fixation implants to restore the bone and soft tissue anatomy toward normalcy.

The sacroiliac joint is located in the lower back at the juncture of the ilium, the upper bone of the pelvis, and the sacrum at the distal end of the spine. While the sacroiliac joint has a limited range of motion, dysfunction of the joint has been identified. The joint is supported by a range of ligaments including, for example, the sacroiliac ligament at the distal end of the joint and the anterior sacroiliac ligament at the top of the joint.

The sacroiliac joint helps transfer energy between the spine, lower limbs, abdomen, and pelvis. It also acts as a shock absorber during physical activities and helps to distribute force throughout the body. Additionally, it helps provide balance and stability while standing or walking, which can help reduce the risk of falls.

The sacroiliac joint connects the two major skeleton parts, the sacrum (lower spine) and the ilium (pelvis). This joint is vital in maintaining balance and mobility, as it provides stability and flexibility to support the body's weight while also providing freedom of movement. It acts as a bridge between the spine and lower extremities, like the legs, which helps maintain upright posture and coordination during physical activities such as walking, running, and jumping. Any disruption or issues with this joint can cause pain and discomfort, which is why it is essential to keep it functioning correctly.

The sacroiliac joint is increasingly being diagnosed as a pain generator. That is, sacroiliac joint degenerative disease and instability are being diagnosed and treated more commonly. Sacroiliac pain may be caused by a disruption in the joint itself, a biomechanical problem like a muscle imbalance, trauma, an inflammatory condition like ankylosing spondylitis, or a degenerative problem as seen with post-lumbar fusion adjacent segment disorder. Other contributing factors include post pregnancy pain/instability, longer life span, and/or more active lifestyles. In addition, complex spine surgeries, such as for correction of sagittal plane deformity, often require iliac fixation to maintain correction in patients with a high pelvic incidence or high risk of lumbo-sacral hardware failure.

The sacroiliac joint is held together by several ligaments, including the sacroiliac ligament at its distal end and the anterior sacroiliac ligament at its top. Additionally, many blood vessels and nerves pass close by this joint on their way to other body parts. So care must be taken when performing any procedures near this sensitive area so as not to damage these vital structures.

The preferred method for locating the sacroiliac joint is from the front. Current art does not disclose an efficient way to find the sacroiliac joint while avoiding the aforementioned vital structures. Therefore, it is desirable for a new and/or improved method to locate the sacroiliac joint.

Current art discloses methods and devices for fusing the sacroiliac joint to the sacrum and ilium using an implant. Because the forces normally absorbed by the sacroiliac joint may exceed the force that the implant can absorb, the implant can shear and create unwanted discomfort. In extreme cases, a new implant may need to be inserted. Many devices penetrate and attempt to affix the sacrum and ilium relative to one another. These devices may comprise a screw penetrating both bones and joining them together in a manner similar to joining two pieces of adjacent wood with a screw. See, for example, U.S. Pat. No. 10,987,144 to Asfora, and U.S. Pat. No. 10,179,014 to Menmuir et al. Another type of device is screwed or forced into a space defined between the sacrum and ilium. See, for example, U.S. Pat. No. 11,045,231 to Stark. Thus, it would be desirable to have an improved intraarticular spacer.

Furthermore, the current techniques and instruments do not allow for a secure and consistent fusion construct. They may provide one or the other many times, but not both issues. This may lead to further sacroiliac joint instability and a failed surgery.

It is therefore desirable to provide new surgical methods and tools for treating damaged sacroiliac joints that securely and consistently fuse the joint—the present invention solves the aforementioned problems.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

The intraarticular spacer is directed to an improved method and device for immobilizing the sacroiliac joint. Immobilization may refer to mechanical holding and/or fusion. The intraarticular spacer generally comprises a body, at least one aperture, at least one anchor, a driver engagement, and an exterior channel.

In one aspect, an intraarticular spacer for stabilizing an ilium and a sacrum at a sacroiliac joint, the intraarticular spacer includes a body defining an exterior surface, a proximal end, and a distal end, and includes at least one aperture, the proximal end smaller than the distal end, the distal end includes a driver engagement, the at least one aperture arranged on the body, at least one anchor on the exterior surface extending from the proximal end to the distal end adapted to engage the sacrum and the ilium, and an exterior channel on the exterior surface of the body.

The intraarticular spacer may also include stabilizing material coupled to the body.

The intraarticular spacer may also include the anchor selected from a thread, a barb, and a ridge.

The intraarticular spacer may also include the body, which further includes a central bore extending longitudinally along a central axis of the body.

The intraarticular spacer may also include the driver engagement being defined by recessed sections.

The intraarticular spacer may also include the central bore tapered in diameter from the distal end to the proximal end.

The intraarticular spacer may also include where an exterior channel having a depth less than the thickness of the body.

The intraarticular spacer may also include where the stabilizing material is selected from bone material and bone immobilizing material.

The intraarticular spacer may also include the anchor comprising a thread on the exterior surface arranged longitudinally about a central axis of the body.

The intraarticular spacer may also include the central bore defining an interior surface and includes an interior thread defined on the interior surface.

The intraarticular spacer may also include the distal end profile selected from a polygon and a circle.

The intraarticular spacer may also include the distal end profile being circular.

The intraarticular spacer may also include the intraarticular spacer comprised of a metal or alloy.

In one aspect, an intraarticular spacer for stabilizing an ilium and a sacrum at a sacroiliac joint, the intraarticular spacer includes a body defining a central bore, an exterior surface, a proximal end, and a distal end. The body includes at least one aperture therethrough, the central bore defining an interior surface and including an interior thread, the interior thread on the interior surface, the proximal end smaller than the distal end and including more than one prong, the distal end including a driver engagement, the at least one aperture arranged on the body, an anchor on the exterior surface adapted to engage the ilium and sacrum at a desired length, and an exterior channel on the exterior surface of the body.

In one aspect, an intraarticular spacer for stabilizing an ilium and a sacrum at a sacroiliac joint, the intraarticular spacer includes a body defining a central bore, an exterior surface, a proximal end, and a distal end and includes at least one aperture, the central bore defining an interior surface and includes an interior thread, the interior thread on the interior surface, the proximal end smaller than the distal end and includes more than one prong, the more than one prong adapted to engage a sacroiliac joint, the distal end includes a driver engagement, the at least one aperture arranged on the body, a thread on the exterior surface extending from the proximal end to the distal end, and an exterior channel on the exterior surface of the body.

In one aspect, an intraarticular spacer for stabilizing an ilium and a sacrum at a sacroiliac joint, the intraarticular spacer includes a cannulated body defining a central bore, an exterior surface, a proximal end, and a distal end, and includes at least one aperture, the central bore extending the length of the cannulated body, defining an interior surface, and includes an interior thread, the interior thread on the interior surface extending from the proximal end to the distal end and arranged helically about the central longitudinal axis of the cannulated body, the proximal end smaller than the distal end and defining more than one prong, the more than one prong adapted to engage the sacroiliac joint, the distal end includes a driver engagement adapted to receive rotational torque from a cooperating driver, the at least one aperture arranged on the cannulated body, an exterior thread on the exterior surface extending from the proximal end to the distal end and arranged helically about a central longitudinal axis of the cannulated body, and an exterior channel on the exterior surface arranged helically about the central longitudinal axis of the cannulated body.

In one aspect, a surgical method of stabilizing an ilium and a sacrum at a sacroiliac joint, the surgical method includes inserting a spinal needle obtaining an arthrogram locating the sacroiliac joint with the arthrogram making a posterior incision cutting the spinal needle at a predetermined location inserting a second needle over the spinal needle inserting a guide-wire over the second needle exchanging the second needle for a the guide-wire inserting a distractor into the sacroiliac joint using a tap inserting the intraarticular spacer in the posterior incision tapping the intraarticular spacer, thereby wedging the intraarticular spacer between the sacrum and the ilium fusing the sacrum and the ilium at the sacroiliac joint.

The surgical method may also include where the intraarticular spacer includes a body defining an exterior surface, a proximal end, and a distal end, and includes at least one aperture, the proximal end smaller than the distal end, the distal end includes a driver engagement adapted to engage a cooperating driver, the at least one aperture arranged on the body, at least one anchor coupled to the exterior surface adapted to engage the sacrum and the ilium, and an exterior channel on the exterior surface of the body, and where the intraarticular spacer is cannulated.

The surgical method may also include adding the step of adding stabilizing material into the central bore before insertion. Other technical features may be readily apparent to one skilled in the art from the following figures, descriptions, and claims.

The surgical method may also include the intraarticular spacer, further includes a central bore. Other technical features may be readily apparent to one skilled in the art from the following figures, descriptions, and claims.

Other technical features may be readily apparent to one skilled in the art from the following figures, descriptions, and claims.

BRIEF DESCRIPTION OF THE DRAWINGS

These and other features, aspects, and advantages of the present invention will become better understood with regard to the following description, appended claims, and accompanying drawings where:

DESCRIPTION

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments, the articles "a," "an," "the" and "said" are intended to mean that there are one or more of the elements. The terms "comprising," "including," "having," and grammatical equivalents thereof are intended to be inclusive and mean that there may be additional elements other than the listed elements.

Moreover, any use of "top," "bottom," "above," "below," other directional terms, and variations of these terms is made for convenience, but does not require any particular orientation of the components.

The term "at least" followed by a number is used herein to denote the start of a range beginning with that number (which may be a range having an upper limit or no upper limit, depending on the variable being defined). For example, "at least 1" means 1 or more than 1.

The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40% means 40% or less than 40-%.

When in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit 100 mm.

In one aspect, an intraarticular spacer for stabilizing an ilium and a sacrum at a sacroiliac joint, the intraarticular spacer includes a body defining an exterior surface, a proximal end, and a distal end, and includes at least one aperture, the proximal end smaller than the distal end, the distal end includes a driver engagement, the at least one aperture arranged on the body, at least one anchor on the exterior surface extending from the proximal end to the distal end adapted to engage the sacrum and the ilium, and an exterior channel on the exterior surface of the body.

Figure 1:
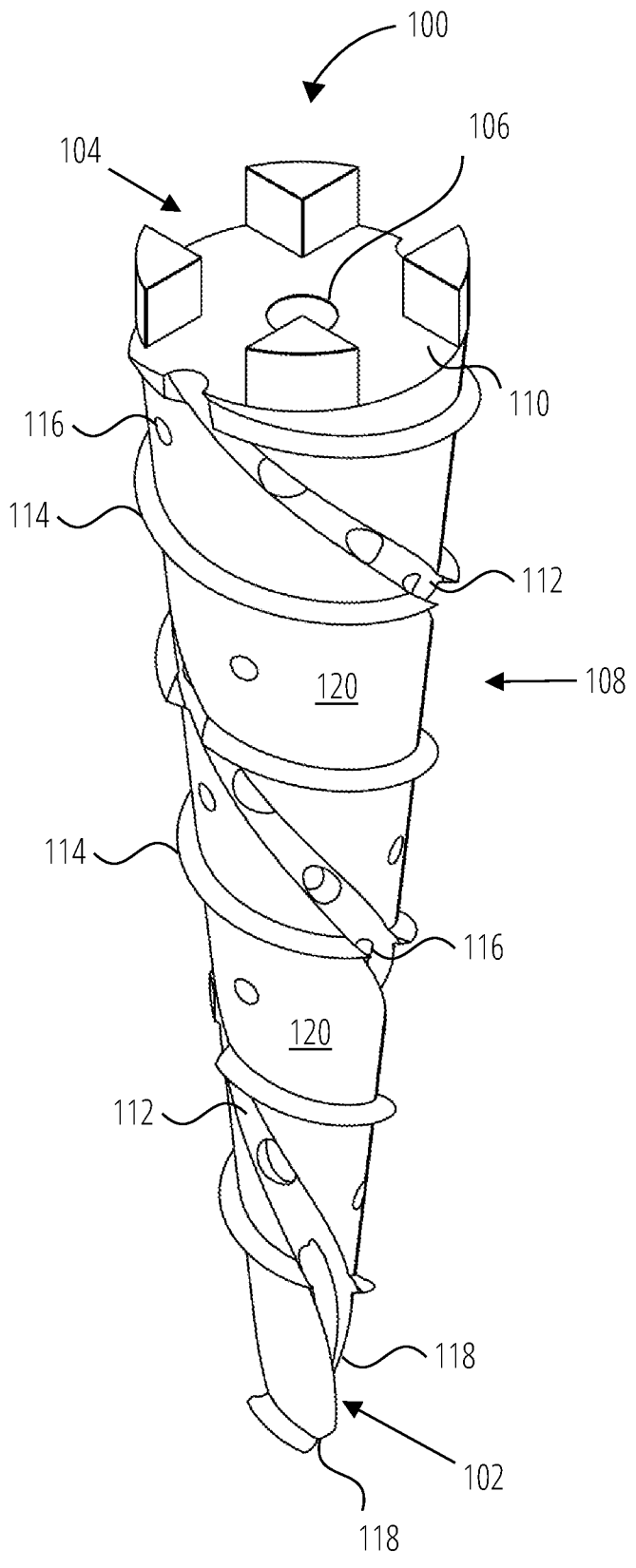
FIG. 1 is a perspective view of the intraarticular spacer in accordance with the embodiment of the present disclosure.

Turning to the present figures, FIG. 1 is a perspective view of one aspect of the intraarticular spacer 100. The intraarticular spacer 100 broadly comprises a body 108 having a proximal end 102, and a distal end 104. In one embodiment, the intraarticular spacer 100 is a circular frustum with the proximal end 102 smaller than the distal end 104, creating a taper along the body 108. It should be appreciated that the body 108 could be another shape to accommodate the sacroiliac joint (later shown in FIG. 7-FIG. 8). For example, the body 108 could be a non-tapered cylinder or a square-based pyramid. Other polygon profiles may be used to define the base of the body at the distal end 104.

In some embodiments, the proximal end 102 comprises more than one prong 118. The proximal end 102 defines two prongs 118. It should be appreciated that the more than two prongs may be used, as shown later in FIG. 7. The prongs 118 are sufficiently defined at the proximal end 102. The prongs 118 are adapted to engage a sacroiliac joint.

In some embodiments, the distal end 104 comprises a driver engagement 110 adapted to receive rotational torque from a cooperating driver. The driver engagement 110 is defined by recessed sections in one embodiment, creating four cooperating surfaces. Other driver engagement 110 profiles well known in the art may be used to acommodate the variety of cooperating drivers. Examples include internal or external hexagon, torx (R), and the like.

The intraarticular spacer 100 further comprises a thread 114. The thread 114 extends longitudinally about a central axis of the body 108 on the exterior surface 120. In one embodiment, thread 114 runs helically around the body 108 from the proximal end 102 to the distal end 104. It should be appreciated that the thread 114 does not have to be continuous. Therefore, the thread 114 does not have to extend the length of the body 108, from the distal end 104 to the proximal end 102. As shown in FIG. 1, the thread 114 has various breaks where the thread 114 intersects with the exterior channel 116 and the at least one aperture 112. The thread 114 has a triangular profile; however, it should be appreciate other thread profiles may be used. Other thread profiles include a multi-tipped polygon. The thread is adapted to engage the ilium and sacrum at the sacroiliac joint.

The exterior channel 116 extends longitudinally about the central axis of the body 108. The exterior channel 116 is recessed and extends helically in the one embodiment. Furthermore, the exterior channel 116. It should be appreciated that the exterior channel 116 does not have to be recessed, extended helically, or continuously. In alternate embodiments of the intraarticular spacer 100, the exterior channel 116 could have one or more breaks or run the length of the body 108 longitudinally from one end to the other. In yet other embodiments, the intraarticular spacer 100 may have one or more exterior channel 116.

The at least one aperture 112 is arranged on the body 108 of the intraarticular spacer 100. In some embodiments at least one aperture 112 is necessary; however, various apertures 112 may be arranged on the body 108. The aperture 112 is a circular bore that extends through a thickness of the body 108. The aperture 112 is not limited to the exterior surface 120 but can intersect the exterior channel 116 and thread 114. As shown in FIG. 1 the apertures 112 are of various sizes, angles, and directions.

Figure 2:
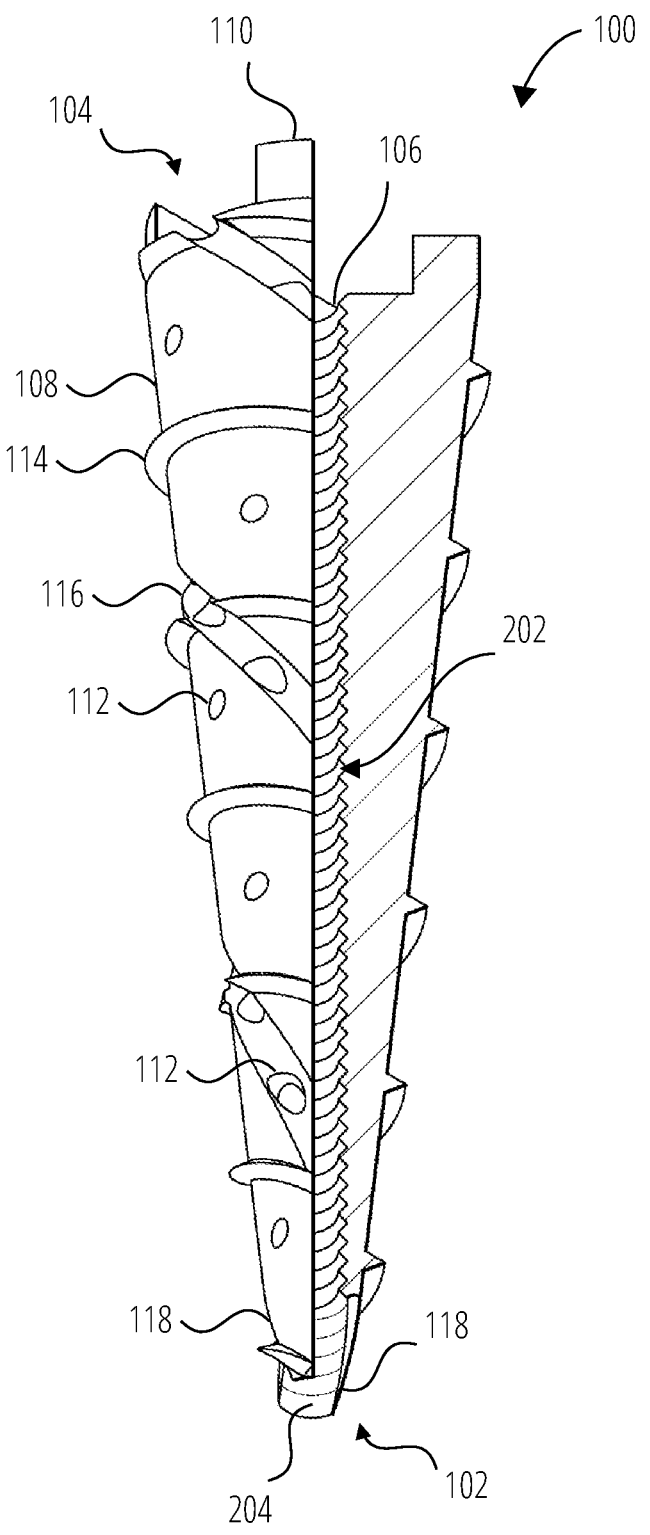
FIG. 2 is a partial cross-section of the intraarticular spacer in accordance with one embodiment of the present disclosure.

In addition, in one embodiment the intraarticular spacer 100 further comprises a central bore 106. FIG. 2 is a partial cross-section view of the intraarticular spacer 100. The central bore 106 is readily apparent from this view. The central bore 106 is cylindrical in shape and extends perpendicular to a central longitudinal axis of the body 108. The length of the central bore 106 is preferably from the proximal end 102 to the distal end 104. The central bore 106 also defines an interior surface 204. The bore is preferably 1.5 mm in diameter. The intraarticular spacer 100 is cannulated by and through the central bore 106. The central bore 106 is to allow the intraarticular spacer 100 to be placed over a guidewire facilitating better alignment prior to drilling or insertion a patient. In some embodiments the central bore 106 may be tapered. For example, the central bore 106 may taper from the distal end 104 to the proximal end 102.

As shown in FIG. 2, an interior thread 202 is coupled on the interior surface 204. The interior thread 202 is a reverse thread arranged longitudinally about a central axis of the body 108 as well. The interior thread 202 is adapted for removal of the intraarticular spacer 100.

Figure 3:
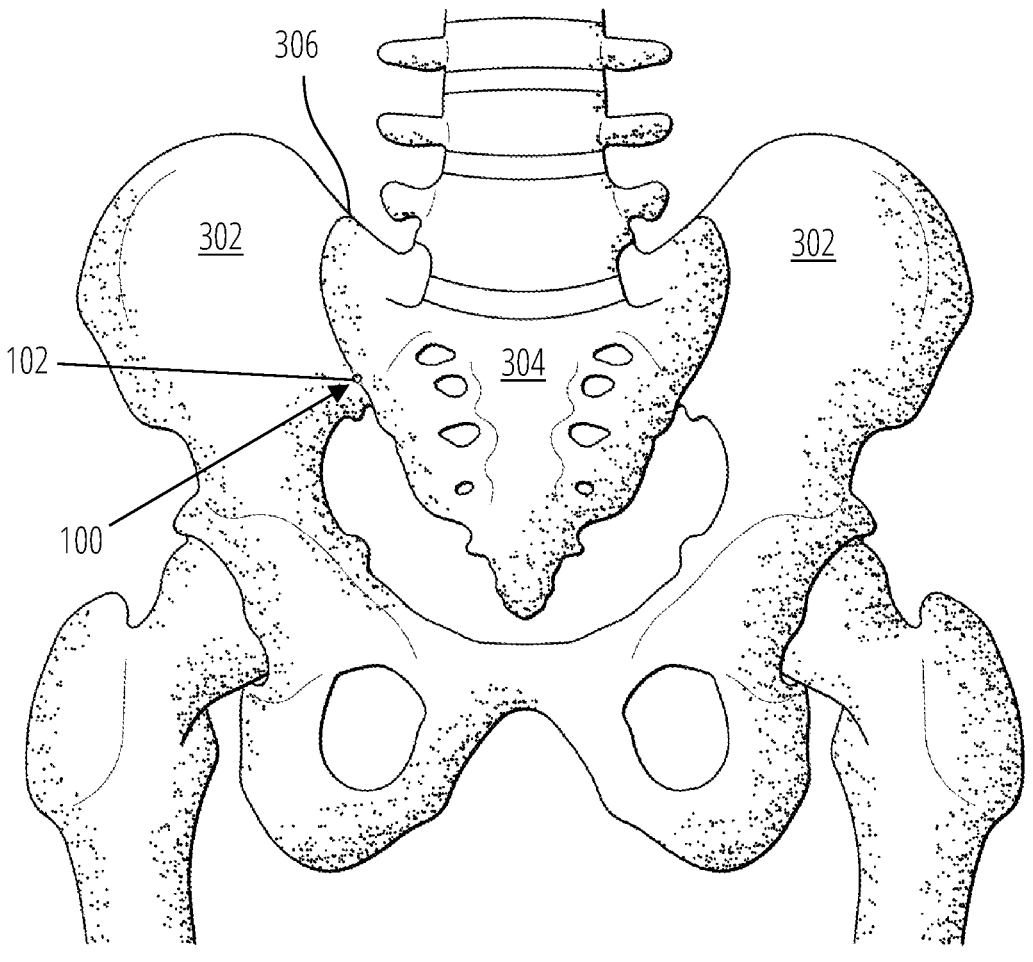
FIG. 3 is a frontal view of the human skeletal system showing the intraarticular spacer placed in the sacroiliac joint.

FIG. 3 is a partial skeletal representation of the mid-portion of a human anatomy. A frontal view, or anterior view, of the human skeletal system showing the proximal end 102 of the intraarticular spacer 100 placed in the sacroiliac joint 306 is shown in FIG. 3. The sacroiliac joint 306 is located in between the ilium 302 and sacrum 304. More specifically the illiac wing, 302, is shown The intraarticular spacer 100 is placed in at the sacroiliac joint 306.

Figure 4:
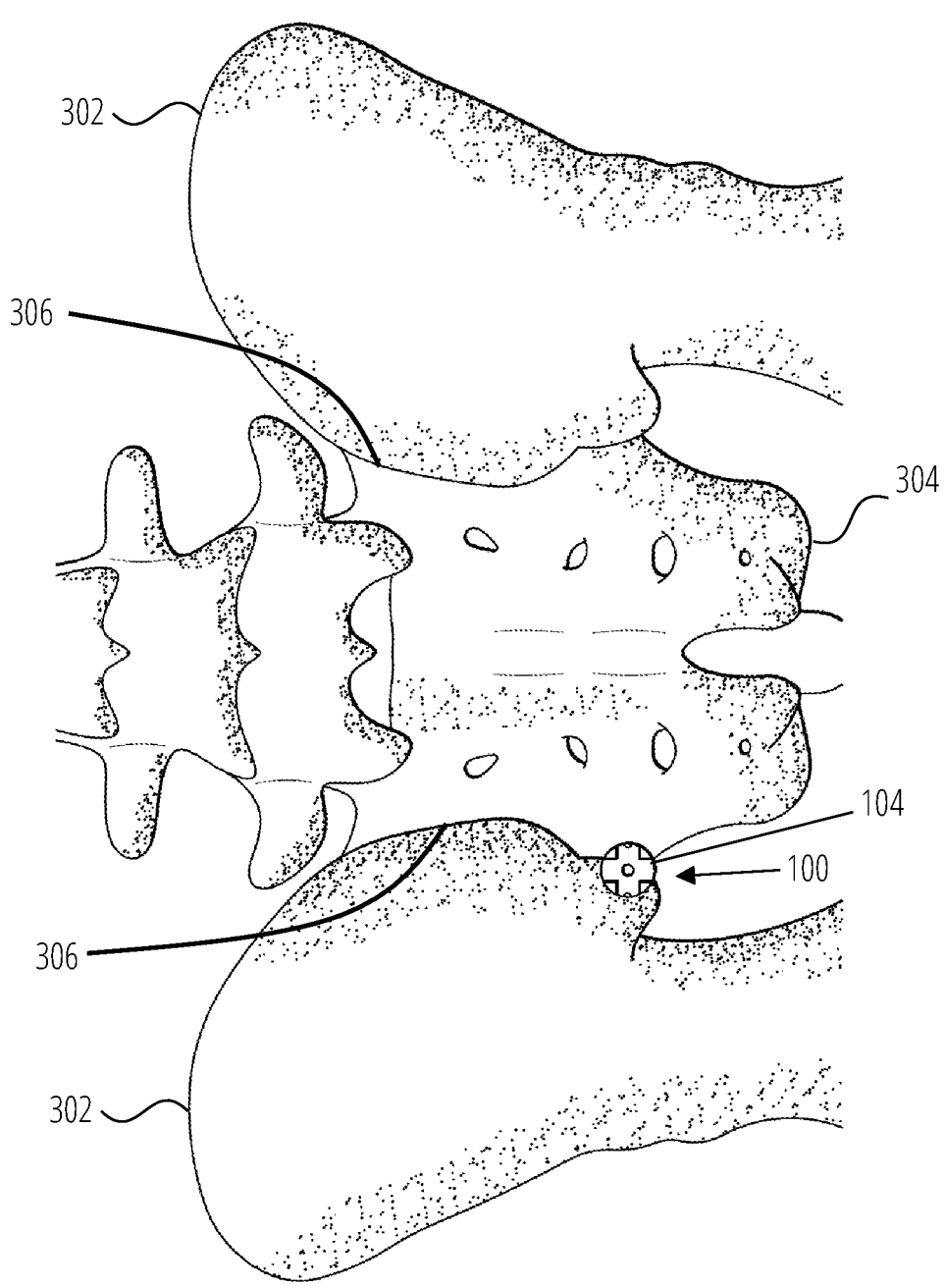
FIG. 4 is a back view of the human skeletal system showing the intraarticular spacer placed in the sacroiliac joint.

FIG. 4 is a back view, or posterior view, of the human skeletal system showing the distal end 104 of the intraarticular spacer 100 placed in the sacroiliac joint 306.

Figure 5:
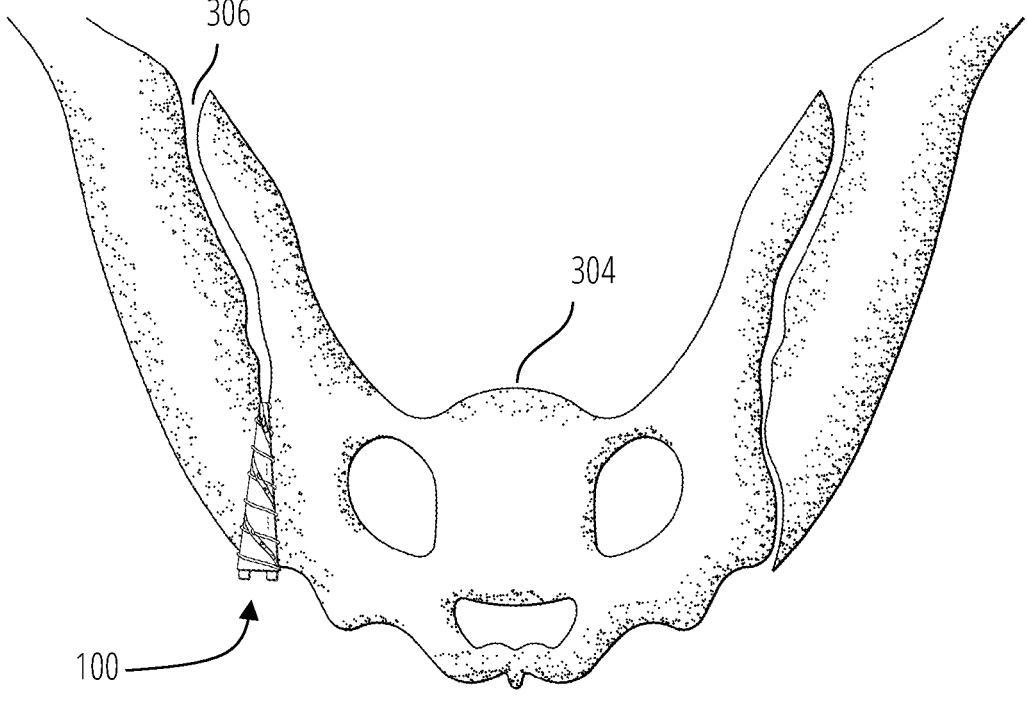
FIG. 5 is a top-down cross-section of the human skeletal system showing the intraarticular spacer placed in the sacroiliac joint.

FIG. 5 is a cross-section of the human skeletal system showing the intraarticular spacer 100 placed in the sacroiliac joint 306. This view clearly shows the thread 114 engaged with the ilium 302 and the sacrum 304 at a desired location.

Figure 6:
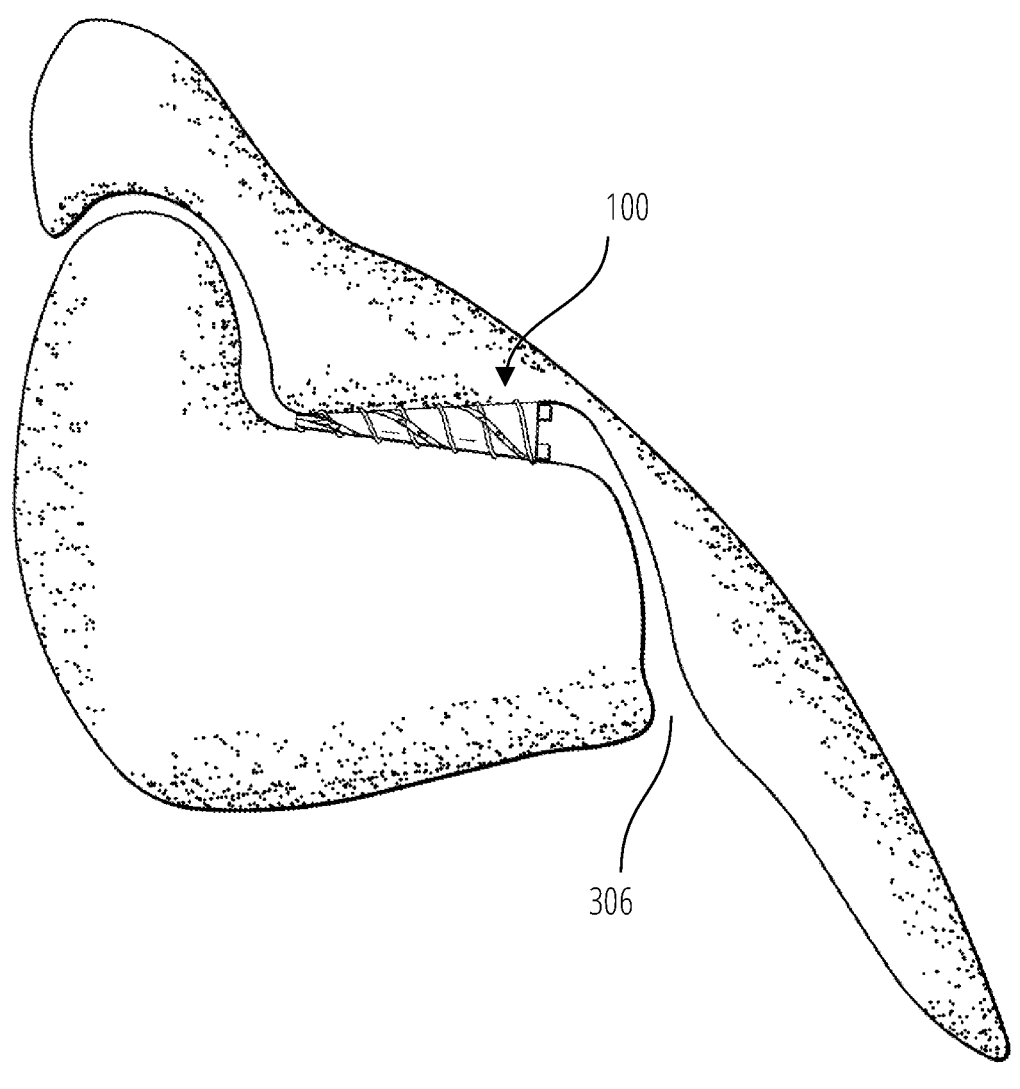
FIG. 6 is a side view of the human skeletal system showing the intraarticular spacer placed in the sacroiliac joint.

FIG. 6 is a side view of the human skeletal system showing the intraarticular spacer 100 placed in the sacroiliac joint 306. This view further illustrates the intraarticular spacer 100 engaged with the ilium 302 and sacrum 304 at the sacroiliac joint 306.

Figure 7:
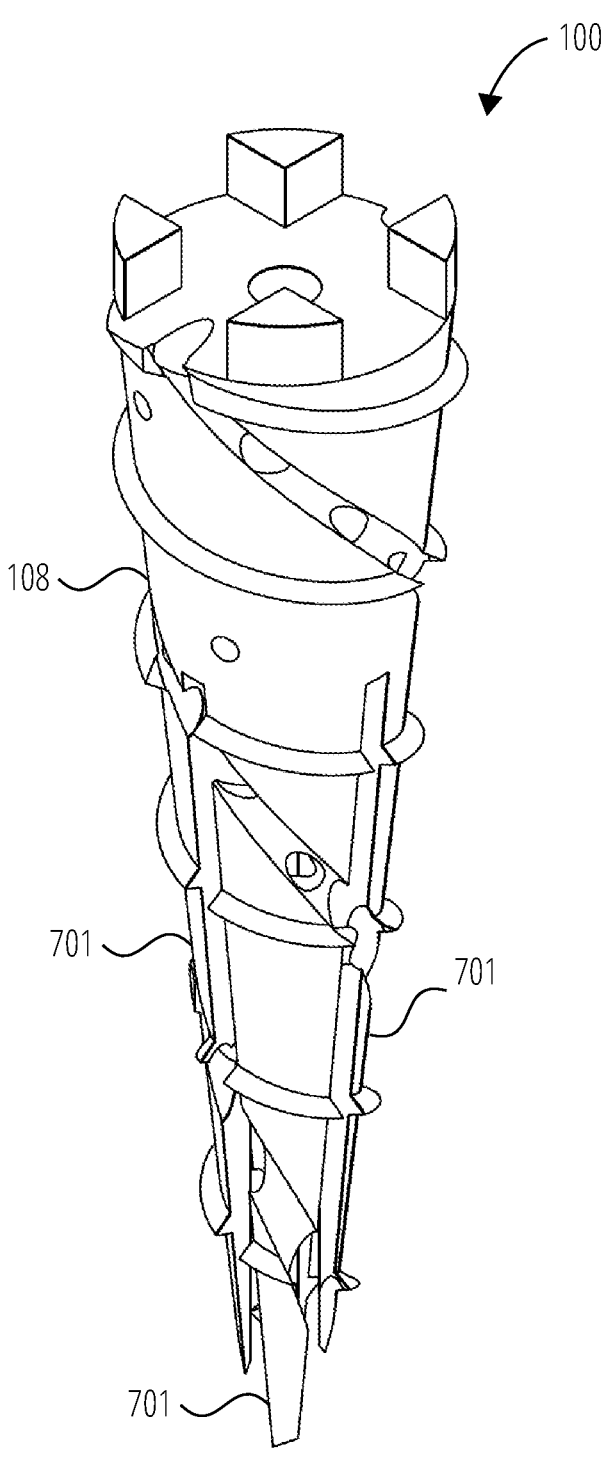
FIG. 7 is an alternate embodiment of the intraarticular spacer.

In a preferred embodiment the overall length of the intraarticular spacer 100 is 30 mm, with the central bore 106 being 1.5 mm in diameter, and the distal end 104 being 7 mm. It should be noted that the dimensions of the intraarticular spacer 100 depend on the length, width, and curvature of the sacroiliac joint 306. Therefore, the prongs 118 are adapted to engage the sacroiliac joint 306 of varying dimensions. An alternate embodiment of the prong is shown in FIG. 7. As shown, the prongs 701 are more defined than the prongs 118 from FIG. 1. The prongs prong 701 extend more than half the length of the body 108. It should be appreciated that the prongs 701 may be of various lengths to sufficiently be adapted to engage the ilium 302 and the sacrum 304 at the sacroiliac joint 306. The prongs 701 intersect the exterior channel 116, the thread 114, and the at least one aperture 112. Because the body 108 is conical, the prongs 701 define the proximal end 102 and are tipped.

Figure 8:
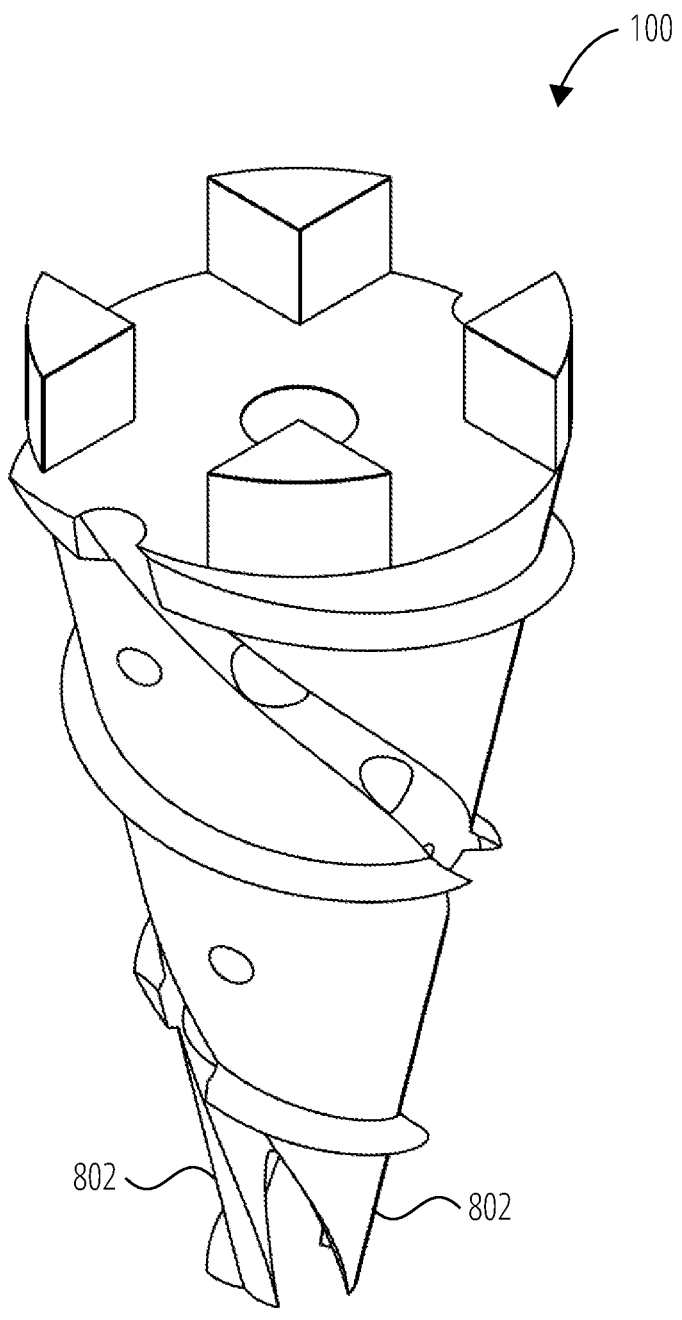
FIG. 8 is yet another alternate embodiment of the intraarticular spacer.

Yet another embodiment is shown in FIG. 8 of the intraarticular spacer 100. Here the prongs 802 are less defined than prongs 701 or prongs 118.

The intraarticular spacer 100 stabilizes the ilium 302 and the sacrum 304 at the sacroiliac joint 306 in the patient. First, a spinal needle is inserted before obtaining an arthrogram to locate the sacroiliac joint. A posterior incision is made on the patient to access the sacroiliac joint 306. The spinal needle is prepared to accept a second needle. A guide-wire is exchanged for the second needle. A distractor is then inserted into the sacroiliac joint 306 using a tap. The intraarticular spacer 100 is inserted into the posterior incision and advanced over the guide-wire. The intraarticular spacer 100 is wedged between the sacrum 304 and the ilium 302 at the sacroiliac joint 306. Preferably, stabilizing material is added into the central bore 106. The intraarticular spacer 100 promotes fusion of the sacrum and the ilium.

Although the present invention has been described in considerable detail with reference to certain preferred versions thereof, other versions are possible. Therefore, the spirit and scope of the appended claims should not be limited to the description of the preferred versions contained herein. Any element in a claim that does not explicitly state "means for" performing a specified function, or "step for" performing a specific function, is not to be interpreted as a "means" or "step" clause as specified in 35 U.S.C § 112, ¶6. In particular, the use of "step of" in the claims herein is not intended to invoke the provisions of 35 U.S.C § 112, ¶6.

LISTING OF DRAWING ELEMENTS 100 intraarticular spacer
102 proximal end
104 distal end
106 central bore
108 body
110 driver engagement
112 aperture
114 thread
116 exterior channel
118 prong
120 exterior surface
202 interior thread
204 interior surface
302 ilium
304 sacrum
306 sacroiliac joint
701 prong
802 prong

What is claimed is:

1. An intraarticular spacer for stabilizing an ilium and a sacrum at a sacroiliac joint, the intraarticular spacer comprising:
   a) a body defining an exterior surface, a proximal end, and a distal end,
      i) the body further defining at least one aperture therethrough,
      ii) the proximal end smaller than the distal end,
      iii) the distal end comprising a driver engagement adapted to engage a cooperating driver,
   b) at least one anchor coupled to the exterior surface adapted to engage the sacrum and the ilium; and
   c) an exterior channel defined on the exterior surface of the body.

2. The intraarticular spacer of claim 1, further comprising more than one prong coupled to the proximal end.

3. The intraarticular spacer of claim 1, further comprising stabilizing material coupled to the body.

4. The intraarticular spacer of claim 3, wherein the stabilizing material selected from a bone material and a bone immobilizing material.

5. The intraarticular spacer of claim 1, the anchor selected from a thread, a barb, and a ridge.

6. The intraarticular spacer of claim 5, the anchor comprising a thread defined on the exterior surface arranged longitudinally about a central axis of the body.

7. The intraarticular spacer of claim 1, wherein the body is cannulated further comprising a central bore extending longitudinally through a central axis of the body.

8. The intraarticular spacer of claim 7, the central bore defining an interior surface and comprising an interior thread coupled to the interior surface.

9. The intraarticular spacer of claim 7, wherein the interior thread consists of a reverse thread adapted for removal of the intraarticular spacer.

10. The intraarticular spacer of claim 1, the driver engagement defined by recessed sections.

11. The intraarticular spacer of claim 10, the profile of the distal end selected from a polygon and a circle.

12. The intraarticular spacer of claim 11, the distal end consisting of a circle profile.

13. The intraarticular spacer of claim 1, the central bore tapered in diameter from the distal end to the proximal end.

14. The intraarticular spacer of claim 1, the intraarticular spacer consisting of a metal or alloy.

15. The intraarticular spacer of claim 1, wherein the depth of the exterior channel is less than a thickness of the body.

16. An intraarticular spacer for stabilizing an ilium and a sacrum at a sacroiliac joint, the intraarticular spacer comprising:

a) a cannulated body defining a central bore, an exterior surface, a proximal end, and a distal end, i) the body further defining at least one aperture therethrough arranged on the cannulated body, ii) the central bore defining an interior surface and comprising an interior thread, the interior thread on the interior surface, iii) the proximal end smaller than the distal end and comprising more than one prong, and iv) the distal end comprising a driver engagement;

b) an anchor on the exterior surface adapted to engage the ilium and sacrum at a desired length; and c) an exterior channel defined on the exterior surface of the cannulated body.

17. An intraarticular spacer for stabilizing an ilium and a sacrum at a sacroiliac joint, the intraarticular spacer comprising:

a) a cannulated body defining a central bore, an exterior surface, a proximal end, and a distal end, and comprising at least one aperture therethrough arranged on the cannulated body, i) the central bore defining an interior surface and comprising an interior thread, the interior thread on the interior surface, ii) the proximal end smaller than the distal end and comprising more than one prong, the more than one prong adapted to engage a sacroiliac joint, iii) the distal end comprising a driver engagement;

b) a thread on the exterior surface extending from the proximal end to the distal end;

c) an exterior channel defined on the exterior surface of the cannulated body.

18. An intraarticular spacer for stabilizing an ilium and a sacrum at a sacroiliac joint, the intraarticular spacer comprising:

a) a cannulated body defining a central bore, an exterior surface, a proximal end, and a distal end, i) at least one aperture arranged on the cannulated body, ii) the central bore extending the length of the cannulated body, defining an interior surface, and comprising an interior thread, the interior thread on the interior surface extending from the proximal end to the distal end and arranged helically about a central longitudinal axis of the cannulated body, iii) the proximal end smaller than the distal end and comprising more than one prong, the more than one prong adapted to engage the sacroiliac joint, iv) the distal end comprising a driver engagement adapted to engage a cooperating driver, and wherein the cannulated body is configured to be inserted into the sacroiliac joint;

b) an exterior thread on the exterior surface extending from the proximal end to the distal end and arranged helically about the central longitudinal axis of the cannulated body; and c) an exterior channel on the exterior surface arranged helically about the central longitudinal axis of the cannulated body, wherein the depth of the exterior channel is less than a thickness of the cannulated body.

19. A surgical method of stabilizing an ilium and a sacrum at a sacroiliac joint, the surgical method comprising:

(a) inserting a spinal needle;

(b) obtaining an arthrogram;

(c) locating the sacroiliac joint with the arthrogram;

(d) making a posterior incision;

(e) cutting the spinal needle at a predetermined location;

(f) inserting a second needle over the spinal needle;

(g) inserting a guide-wire over the second needle;

(h) exchanging the second needle for the guide-wire;

(i) inserting a distractor into the sacroiliac joint;

(j) using a tap;

(k) inserting an intraarticular spacer in the posterior incision;

(l) tapping the intraarticular spacer, thereby wedging the intraarticular spacer between the sacrum and the ilium; and (m) fusing the sacrum and the ilium at the sacroiliac joint.

20. The surgical method of claim 19, wherein the intraarticular spacer comprises a cannulated body defining a central bore, an exterior surface, a proximal end, and a distal end, and defining at least one aperture therethrough, the proximal end smaller than the distal end, the distal end comprising a driver engagement adapted to engage a cooperating driver;

at least one anchor coupled to the exterior surface adapted to engage the sacrum and the ilium; and an exterior channel on the exterior surface of the cannulated body.

21. The surgical method of claim 19, adding the step of adding stabilizing material into the central bore before insertion.

* * * * *